United States Patent
Ghosh et al.

(10) Patent No.: US 7,576,026 B2
(45) Date of Patent: Aug. 18, 2009

(54) METHOD OF HYDROTHERMAL TREATMENT OF PHOSPHORUS-MODIFIED ZEOLITE CATALYTS

(75) Inventors: Ashim Kumar Ghosh, Houston, TX (US); Neeta Kulkarni, Houston, TX (US); Pamela Harvey, Missouri City, TX (US); Roncalli J. Twomey, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 8 days.

(21) Appl. No.: 11/857,728

(22) Filed: Sep. 19, 2007

(65) Prior Publication Data

US 2008/0009406 A1 Jan. 10, 2008

Related U.S. Application Data

(62) Division of application No. 11/122,919, filed on May 5, 2005, now Pat. No. 7,304,194.

(51) Int. Cl.
*B01J 29/06* (2006.01)
*B01J 29/40* (2006.01)
(52) U.S. Cl. .......................... 502/77; 502/60
(58) Field of Classification Search .............. 502/60, 502/77
See application file for complete search history.

(56) References Cited

U.S. PATENT DOCUMENTS

| | | | |
|---|---|---|---|
| 3,965,207 A | 6/1976 | Weinstein | |
| 4,326,994 A | 4/1982 | Haag et al. | |
| 4,522,929 A | 6/1985 | Chester et al. | |
| 4,548,914 A | 10/1985 | Chu | |
| 4,559,314 A | 12/1985 | Shihabi | |
| 4,590,321 A | 5/1986 | Chu | |
| 4,623,530 A | 11/1986 | Cullo et al. | |
| 4,623,533 A | 11/1986 | Young | |
| 4,638,106 A | 1/1987 | Pieters et al. | |
| 4,665,251 A | 5/1987 | Chu | |
| 4,670,616 A | 6/1987 | De Simone et al. | |
| 4,673,767 A | 6/1987 | Nimry et al. | |
| 4,694,114 A | 9/1987 | Chu et al. | |
| 4,695,666 A | 9/1987 | Chao et al. | |
| 4,695,667 A | 9/1987 | Sumitani et al. | |
| 4,704,495 A | 11/1987 | Dessau | |
| 4,716,135 A | 12/1987 | Chen | |
| 4,721,827 A | 1/1988 | Cullo et al. | |
| 4,727,209 A | 2/1988 | Chao | |
| 4,746,763 A | 5/1988 | Kocal | |
| 4,758,328 A | 7/1988 | Young | |
| 4,761,513 A | 8/1988 | Steacy | |
| 4,847,223 A | 7/1989 | Le Van Mao et al. | |
| 4,861,930 A | 8/1989 | Cottrell et al. | |
| 4,873,067 A | 10/1989 | Valyocsik et al. | |
| 4,891,197 A | 1/1990 | Derouane et al. | |
| 4,891,467 A | 1/1990 | Sikkenga | |
| 4,902,406 A | 2/1990 | Valyocsik | |
| 4,912,073 A | 3/1990 | Chu | |
| 4,914,067 A | 4/1990 | Pellet et al. | |
| 4,935,574 A | 6/1990 | D'Amore et al. | |
| 4,962,255 A | 10/1990 | Fraenkel et al. | |
| 4,973,781 A | 11/1990 | Valyocsik et al. | |
| 5,041,402 A | 8/1991 | Casci et al. | |
| 5,043,502 A | 8/1991 | Martindale et al. | |
| 5,047,141 A | 9/1991 | Chu | |
| 5,068,483 A | 11/1991 | Barthomeuf et al. | |
| 5,094,995 A | 3/1992 | Butt et al. | |
| 5,105,047 A | 4/1992 | Waller | |
| 5,108,579 A | 4/1992 | Casci | |
| 5,110,776 A | 5/1992 | Chitnis et al. | |
| 5,124,299 A | 6/1992 | Waller | |
| 5,171,921 A | 12/1992 | Gaffney et al. | |
| 5,173,461 A | 12/1992 | Absil et al. | |
| 5,178,748 A | 1/1993 | Casci et al. | |
| 5,231,064 A | 7/1993 | Absil et al. | |
| 5,233,102 A | 8/1993 | Butt et al. | |
| 5,246,688 A | 9/1993 | Faust et al. | |
| 5,248,841 A | 9/1993 | Young | |
| 5,254,767 A | 10/1993 | Dwyer | |
| 5,254,770 A | 10/1993 | Olson et al. | |
| 5,294,578 A | 3/1994 | Ho et al. | |
| 5,315,033 A | 5/1994 | Butt et al. | |
| 5,318,696 A | 6/1994 | Kowalski | |

(Continued)

FOREIGN PATENT DOCUMENTS

| | | |
|---|---|---|
| WO | WO94/27934 | 12/1994 |
| WO | WO2006/127827 | 12/2006 |
| WO | WO2007/076088 | 7/2007 |

OTHER PUBLICATIONS

Kaeding, W.W., et al., Selective Alkylation of Toluene to Produce para-Xylene, Journal of Catalysis 67, 1981, pp. 159-174.

Nirula, S.C., Para-Xylene From Toluene and Methanol, Process Economics Program, 1983, pp. 1-23, SRI International, Menlo Park, CA.

*Primary Examiner*—Elizabeth D Wood
(74) *Attorney, Agent, or Firm*—Grady K. Bergen; Jim D. Wheelington; Griggs Bergen LLP

(57) ABSTRACT

A method of treating a ZSM-5-type zeolite catalyst is carried out by treating a ZSM-5 zeolite catalyst having a silica/alumina mole ratio of at least about 200 with a phosphorus compound. The phosphorus-treated ZSM-5 zeolite catalyst is calcined and steamed. Steaming of the catalyst is carried out at a temperature of less than about 300° C. The phosphorus-treated ZSM-5 zeolite catalyst has less than 0.05% by weight of the catalyst of any other element other than phosphorus provided from any treatment of the ZSM-5 zeolite with a compound containing said other element. The catalyst may be used in aromatic alkylation by contacting the catalyst with feed of an aromatic hydrocarbon and an alkylating agent within a reactor under reactor conditions suitable for aromatic alkylation. Water cofeed may be introduced water into the reactor during the aromatic alkylation reaction.

7 Claims, 1 Drawing Sheet

U.S. PATENT DOCUMENTS

| | | |
|---|---|---|
| 5,321,183 A | 6/1994 | Chang et al. |
| 5,336,478 A | 8/1994 | Dwyer et al. |
| 5,345,021 A | 9/1994 | Casci et al. |
| 5,348,643 A | 9/1994 | Absil et al. |
| 5,349,113 A | 9/1994 | Chang et al. |
| 5,349,114 A | 9/1994 | Lago et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,902,919 A | 5/1999 | Chen et al. |
| 5,905,051 A | 5/1999 | Wu et al. |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,251,263 B1 | 6/2001 | Hatanaka et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Verduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,589,901 B2 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 2005/0070749 A1 | 3/2005 | Ghosh et al. |

METHOD OF HYDROTHERMAL TREATMENT OF PHOSPHORUS-MODIFIED ZEOLITE CATALYTS

This application is a division of U.S. patent application Ser. No. 11/122,919, entitled "Hydrothermal Treatment of Phosphorus-Modified Zeolite Catalysts," filed May 5, 2005, now U.S. Pat. No. 7,304,194, which is herein incorporated by reference in its entirety.

TECHNICAL FIELD

The invention relates generally to the alkylation of aromatic compounds and catalysts used for such alkylation.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

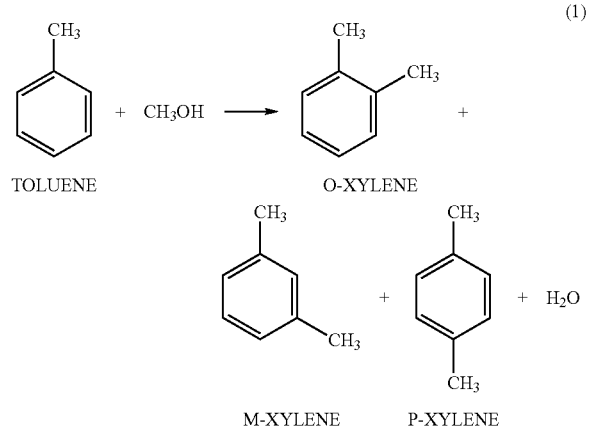

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Byproducts such as C9+ and other aromatic products can be produced by secondary alkylation of the xylene product.

Para-xylene can be separated from mixed xylenes by a cycle of adsorption and isomerization. Such cycle may have to be repeated several times because of the low isomeric concentration in the equilibrium mixture. A high purity grade (99+%) p-xylene is desirable for its oxidation to terephthalic acid. The production cost for such a high purity grade p-xylene can be very high, however. A different method that employs crystallization techniques can be used and may be less expensive where the concentration of p-xylene is around 80% or higher in the initial xylene product. Thus, higher than equilibrium concentrations of p-xylene may be desirable.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

In Kaeding, et al, *Selective Alkylation of Toluene with Methanol to Produce para-Xylene*, Journal of Catalysis, Vol. 67, pp. 159-174 (1981), a procedure of making a ZSM-5 catalyst by incorporating 5% phosphorus was described in which the catalyst was impregnated with a solution of diphenylphosphinous acid in toluene. The ZSM-5 catalyst thus modified showed toluene methylation activity with 84-90% para isomer in the xylene product. In another procedure, a catalyst was modified by incorporating 8.51% phosphorus from an aqueous phosphoric acid reagent. The catalyst showed p-xylene selectivity as high as 97%, however, the catalyst showed a decreasing activity within hours due to coke deposition.

Unfortunately, there are a number of technical hurdles for toluene methylation to be commercially successful and improvements are needed.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
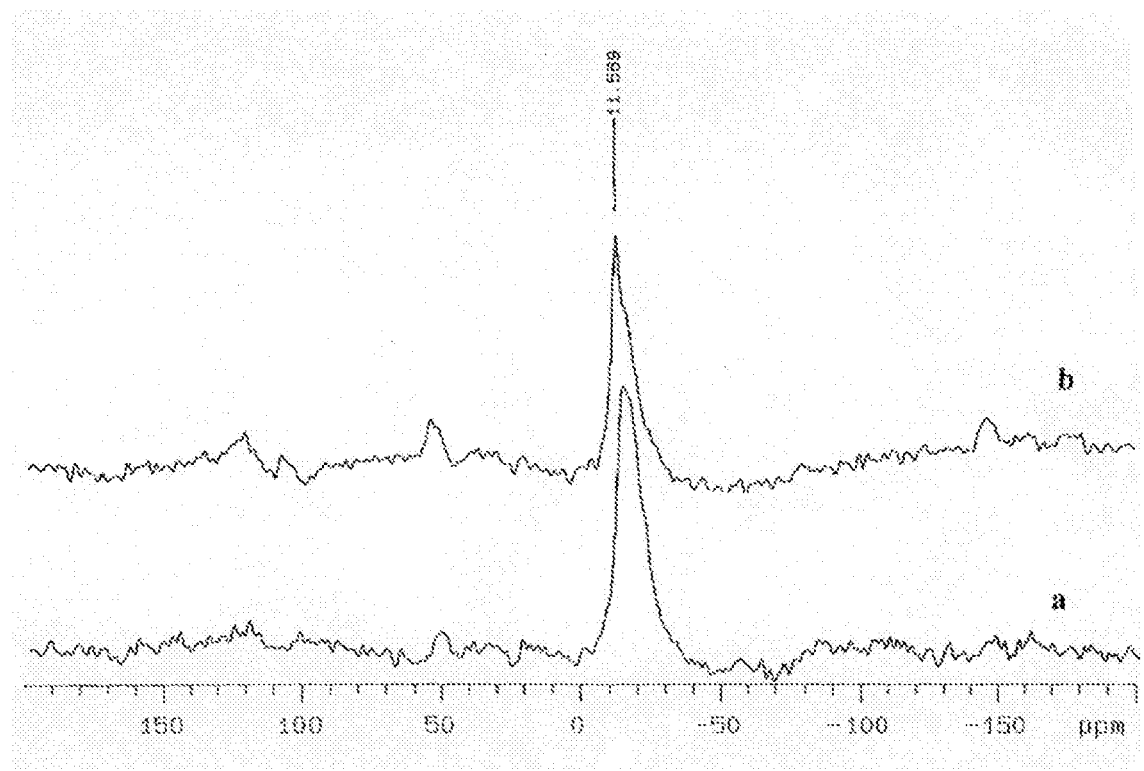
FIG. 1 shows $^{27}$Al MAS NMR spectra of a P-modified ZSM-5 before steaming (spectrum a) and after steaming at 610° C. for 13 days (spectrum b).

Modification of ZSM-5-type zeolite catalysts with phosphorus-containing compounds has been shown to yield significantly greater amounts of p-xylene than the thermodynamic equilibrium value in toluene methylation using unmodified catalysts. Such modification has been shown to provide selectivity for p-xylenes of greater than 80%. Although such phosphorus-treated ZSM-5 catalysts may have a high selectivity for p-xylene, they tend to deactivate at a very fast rate, for example, the catalyst may lose greater than 50% of its initial activity within a day. This may possibly be due to coke deposition on the catalyst.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense. As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for mixed-xylenes may be expressed as:

$$\text{Mole \% Mixed Xylene Selectivity} = [X_{mx}/(T_i - T_o)] \times 100 \quad (3)$$

where, $X_{mx}$ is the number of moles of total (o-, m- or p-) xylenes in the product. As used herein, selectivity for p-xylene may be expressed as:

$$\text{Mole \% p-Xylene Selectivity} = (X_p/X_{mx}) \times 100 \qquad (4)$$

where, $X_p$ is the number of moles of p-xylene.

As used herein, selectivity for methanol may be expressed as:

$$\text{Mole \% Methanol Selectivity} = [X_{mx}/(M_i - M_o)] \times 100 \qquad (5)$$

where, $X_{mx}$ is the number of moles of mixed-xylenes, $M_i$ is the number of moles of methanol fed and $M_o$ is the number of moles unreacted methanol.

The ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of from 200 or more, more particularly from about 250 or more, and still more particularly from about 280 to about 1000 or more, prior to modification. The zeolite may have a crystal particle size of 0.5 micron or more, more particularly from about 0.5 to about 5.0 microns, and still more particularly from about 0.5 to 1.0 microns. The starting ZSM-5 zeolite may be a $NH_4$-ZSM-5 zeolite or an H-ZSM-5 zeolite, or other cation-exchanged ZSM-5 zeolite.

The ZSM-5 zeolite may be modified by treating with phosphorus (P)-containing compounds. Such modified catalysts may be treated to provide a phosphorus content in an amount of from about 0.01 g P/g zeolite or more, more particularly from about 0.08 to about 0.15 g P/g zeolite, still more particularly from about 0.09 to about 0.13 g P/g zeolite. Such phosphorus-containing compounds may include, for example, phosphonic, phosphinous, phosphorus and phosphoric acids, salts and esters of such acids and phosphorous halides. In particular, phosphoric acid ($H_3PO_4$) and ammonium hydrogen phosphate (($NH_4$)$_2HPO_4$) are particularly well suited for use as the phosphorus-containing compound to provide a catalyst for toluene methylation with shape selective properties to give high p-xylene concentration.

The phosphorus treatment may be carried out by various techniques. This may include slurry evaporation and wet incipient methods. In slurry evaporation, the phosphorus may be incorporated into the catalyst by preparing an aqueous slurry of the zeolite and an aqueous solution of the phosphorus compound. Heating of the slurry may be used to facilitate treatment of the zeolite and evaporation of liquids. Heating of the slurry to temperatures of 70° C. and higher is suitable. The slurry may also be stirred or agitated during this step to ensure uniform treatment. Heating the zeolite slurry to near complete evaporation of the liquid causes the formation of dough which can be dried or calcined to form powder or chunks.

In the wet incipient method, an aqueous solution of the phosphorus compound is added, such as by spraying, to dry the zeolite without forming a slurry. The dry zeolite, which may be initially in the form of a powder, may be mixed with the phosphorus compound to form a dough. If necessary, water may be added to the mixture to facilitate formation of the zeolite dough. The dough may then be dried or calcined to obtain the phosphorus-modified zeolite powder or particles.

It should be noted that the ZSM-5 zeolite structurally contains Al, Si and O, and may contain no or only trace amounts of any other element (egs. B, Be, Ca, Cd, Co, Fe, Mg, etc.) other than phosphorus, including any elements of Groups IA, IIA, IIIA, IVA, VA, VIA, VIIA, VIIIA, IB, IIB, IIIB, IVB or VB of the Periodic Chart of the Elements that serve to enhance the para-selectivity properties of the catalyst. The ZSM-5 zeolite may undergo no treatment to provide any other such elements other than phosphorus to enhance the para-selective properties of the catalyst. If an element other than phosphorus is provided from any such treatment, the ZSM-5 zeolite may contain less than 0.05% by weight of the catalyst of such element, more particularly, less than 0.01% by weight of the catalyst of such element, and still more particularly less than 0.001% by weight of the catalyst of such element.

The catalyst may be bound or unbound. Examples of suitable binders include such materials as alumina, clay, and silica. Those techniques used for preparing the bound catalyst are well known in the art. The phosphorus-modified zeolite catalyst, bound or unbound, may be calcined at a temperature of 400° C. or more in an environment containing oxygen, typically air. Calcining may take place over time, typically from several minutes to one hour or more. Calcining may also take place by gradually increasing the temperature over time.

The calcined P-modified ZSM-5 zeolite may have a BET surface area of 150-200 $m^2$/g determined by $N_2$ adsorption techniques. The total pore volume may be in the range of 0.10-0.18 ml/g catalyst. The catalyst may have acidity showing broad peak(s) with peak maxima between 250° C. and 350° C., as characterized by ammonia temperature programmed desorption ($NH_3$-TPD) technique.

The phosphorus-treated ZSM-5 zeolite catalyst is steamed at low or mild temperatures. The steaming may occur by contacting the zeolite catalyst with steam in the presence of hydrogen gas or air, or other inert gas. Steaming temperatures may range from about 150° C. to about 250° C., 300° C. or 350° C. This may be accomplished separately or in situ within the reactor, prior to any aromatic alkylation reaction or introduction of any reaction feed. Steaming may be carried out by contacting the catalyst in the presence of hydrogen or air or other inert gas. Steaming may be conducted from a few minutes to several hours. Such steaming of the phosphorus treated ZSM-5 zeolite causes no removal of aluminum (Al) from the zeolite framework as evidenced by $^{27}Al$ MAS NMR study.

Where phosphorus-treated ZSM-5 zeolite catalysts have been steamed according to the present invention, increased catalyst activity and selectivity for the catalyst in aromatic alkylation reactions has been observed. This is compared to the same phosphorus-treated ZSM-5 zeolite catalyst used under the same or similar reaction conditions that has not been steamed or where steaming is conducted at higher temperatures. Increases in para-selectivity have been observed, as well as increases in selectivity of the alkylating agent. In particular, significant increases in methanol selectivity have been observed for the catalyst when used in toluene methylation reactions.

Further increases in selectivity and catalyst activity of the mildly steamed phosphorus-modified ZSM-5 zeolite catalyst can also be achieved by additionally introducing water or steam into the reactor as cofeed during the alkylation reaction. Such introduction of steam during the reaction has been described in copending U.S. patent application Ser. No. 10/675,780, filed Sep. 30, 2003, which is herein incorporated by reference. The water introduced into the reactor may be fed into the reactor at a ratio of from about 0.1 or more, and may be less than about 10 moles water per mole of aromatic hydrocarbon and alkylating agent, more particularly, from about 0.3 to about 5, 6 or 7 moles water per mole of aromatic hydrocarbon and alkylating agent. In certain instances, the water may be fed at a ratio of from about 0.2 to 1.2 moles water per mole of aromatic hydrocarbon and alkylating agent, more particularly, from about 0.3 to about 0.9 mole water per mole of aromatic hydrocarbon and alkylating agent. The addition of water (or steam) as cofeed may be done in combination with or without hydrogen cofeed or with the introduction of any inert gas. The water cofeed may be fed into the reactor wherein the conditions are such that substantially no structural aluminum loss of the catalyst results due to the presence of such additional water within the reactor.

In carrying out the aromatic alkylation reactions with the P-modified ZSM-5 catalyst with or without catalyst steaming and both with and without water cofeed, the toluene and methanol feed may be premixed prior to introduction into the reactor as a single mixed feed stream. The feed may also contain small quantities of water, C9+ aromatics and other compounds. The liquid hourly space velocities presented herein, however, are based upon a toluene/methanol feed without the inclusion of any other components. The toluene/methanol molar ratio in the feed can range from 0.5 to 10.0, more particularly 1.0 to 5.0. Optionally, a cofeed gas can be added with the toluene/methanol and steam. The cofeed gas may include hydrogen, nitrogen, helium or other inert gas. The cofeed gas may be provided at a molar ratio of less than about 10 with respect to toluene and methanol. The reactor temperature used herein referred as catalyst bed inlet temperature and a reactor temperature between 400° C. and 700° C. is provided.

The reactor inlet pressure may remain generally constant during the catalytic test run. The reactor inlet pressure may be about 10 psig or more.

The reaction may be carried out in a fixed bed, continuous flow-type reactor in a down flow mode. Single or multi reactors in series and/or parallel are suitable for carrying out the reaction. The reactor temperature can be gradually increased. Initially, upon introduction of feed into the reactor, the reactor temperature may be about 200° C. or above. The temperature may then be increased to the desired temperature. This temperature may be increased gradually at a rate of from about 0.1° C./min to about 10° C./min to provide a temperature of from about 400° C. to about 700° C.

The following examples better serve to illustrate the invention.

EXAMPLES

Using the procedure described below, phosphorus treated zeolite Catalysts A, B, and C were prepared using ZSM-5 zeolite powder as starting material. Phosphoric acid was used to treat the zeolite. The starting zeolite powder was a $NH_4$-ZSM-5 zeolite powder having a $SiO_2/Al_2O_3$ mole ratio of about 280. The crystal particle size of the starting zeolite powder was from about 0.5 to 1.0 micron.

Catalyst A

A phosphorus-modified ZSM-5 catalyst was made by a slurry method as follows. A slurry containing 450.0 g of $NH_4$-ZSM-5 zeolite and 900 ml of deionized water was prepared in a 2000 ml beaker. The beaker was placed on a hot plate and the zeolite suspension was stirred using a mechanical (overhead) stirrer at 250-300 rpm. The temperature of the suspension was slowly raised to about 80-85° C. at which time phosphoric acid was added slowly. Phosphoric acid in an amount of 205.2 g (85 wt % in aqueous) was added to the slurry. The slurry temperature was further increased to between 95-100° C. and heating was continued until all liquid was evaporated to form a dough. The phosphoric-acid modified zeolite was calcined in a convection oven in air at the following temperature program: 90° C. to 120° C. for four hours; at 340° C. to 360° C. for three hours; and 520° C. to 530° C. under air for 10 hours. The calcined zeolite was then crushed and sized using 20 and 40 mesh screens. The phosphorus-modified ZSM-5 zeolite catalyst contained 9.01 g P/g zeolite.

Catalyst B

A phosphorus-modified ZSM-5 catalyst was made by impregnation method as follows. Zeolite powder in an amount of 50.01 g was placed in a 500 ml beaker. To this was slowly added 22.68 g of $H_3PO_4$ acid (85% in aqueous) while mixing vigorously. Water was sprayed to moisten the zeolite powder and to form a dough. The catalyst dough was transferred to a ceramic dish and was calcined in a convection oven in air at the following temperature program: 90° C. to 120° C. for four hours; at 340° C. to 360° C. for three hours; and 510° C. to 530° C. under air for 10 hours. The calcined zeolite was then crushed and sized using 20 and 40 mesh screens. The phosphorus-modified ZSM-5 zeolite catalyst contained 9.02 g P/g zeolite.

Catalyst C

A phosphorus-modified ZSM-5 bound catalyst was prepared as follows. A slurry containing 450.0 g of $NH_4$-ZSM-5 zeolite and 900 ml of deionized water was prepared in a 2000 ml beaker. The beaker was placed on a hot plate and the zeolite suspension was stirred using a mechanical (overhead) stirrer at 250-300 rpm. The temperature of the suspension was slowly raised to about 80-85° C. at which time phosphoric acid was added slowly. A weighted 205.2 g of phosphoric acid (85 wt % in aqueous) was added to the slurry. The slurry temperature was further increased to between 95-100° C. and heating was continued until all liquid was evaporated to form a dough. The phosphoric-acid modified zeolite was calcined in a convection oven in air at the following temperature program: 90° C. to 120° C. for four hours; 340° C. to 360° C. for three hours; and 510° C. to 520° C. under air for 10 hours. A part of the calcined zeolite was then crushed and was sieved using 80 mesh screen. The P/ZSM-5 catalyst contained 9.36 g P/g zeolite. The powder P/ZSM-5 was bound with 10 wt % alumina (commercial grade alumina, Alcoa, HiQ-40, pseudo-boehmite type alumina). The alumina was first peptized with nitric acid (3:1 wt ratio) and then mixed with the P/ZSM-5 powder and mixed vigorously and sprayed with water to form a dough. The dough was calcined by using the same calcination temperature profile used for the P/ZSM-5. The calcined zeolite was then crushed and sized using 20 and 40 mesh screens for testing for reactions. The bound catalyst contained 8.4 g P/g catalyst.

Example 1-4

Catalyst A was used in toluene methylation. A catalyst charge of 5.4 ml of Catalyst A was placed within a ½-inch tubular reactor at about its midpoint. Layers of silicon carbide (SiC) were added to both ends of the catalyst bed. The reactor was tested for leaks in the system at 60-80 psig. The catalyst was then dried at 200° C. under $H_2$ flow for at least one hour before use. In Examples 1 and 3, the reactor feed was introduced without any further catalyst pretreatment, that is, without catalyst pre-steaming. In Examples 2 and 4, however, in order to examine the effect of catalyst steaming, the catalyst was first dried and then was steamed by flowing hydrogen gas containing $H_2O$ (10-12 mole %) at 200° C. overnight. The feed was made by mixing toluene and methanol at a molar ratio of 4.5. The pre-mixed toluene/methanol liquid feed were introduced at a LHSV of 2.0-2.1 $hr^{-1}$. Where water was optionally added to the reactor feed, the water was introduced at a $H_2O$/(toluene+methanol) molar ratio of 0.8 (see Examples 2 and 4). Hydrogen gas was added to the feed at a predetermined rate to maintain a selected $H_2$/(toluene+methanol) molar ratio of 7-8. The catalyst bed inlet temperature was raised to approximately 550° C. When catalyst performance reached steady conditions, conversion and selectivity were calculated using Equations 2-4. Conversion and selectivity obtained in Examples 1-4 are presented below in Table 1.

TABLE 1

| Conversion/Selectivity, mole % | Example 1 Catalyst A, Non-steamed, No cofeed H₂O | Example 2 Catalyst A, Non-steamed, Cofeed H₂O | Example 3 Catalyst A, Steamed at 200° C., No cofeed H₂O | Example 4 Catalyst A, Steamed at 200° C., Cofeed H₂O |
|---|---|---|---|---|
| $X_{Toluene}$ | 3.0 | 11.4 | 10.4 | 13.6 |
| $S_{Mixed-Xylenes}$ | 95.0 | 96.6 | 94.9 | 96.6 |
| $S_{P-Xylene}$ | 80.4 | 90.3 | 84.2 | 89.8 |
| $S_{Methanol}$ | 33.7 | 60.8 | 56.7 | 67.4 |

Examples 5-6

The effect of catalyst steaming temperature was examined on Catalyst A. In all cases, the catalyst was first dried at 200° C., for an hour under hydrogen gas flow. The catalyst was then steamed overnight by flowing hydrogen gas containing from 10-12 mole % H₂O at either 200° C., 300° C. or 500° C. The same reaction conditions as those of Example 4 were used. The results are summarized in Table 2 below.

TABLE 2

| Conversion/Selectivity, mole % | Example 4 Catalyst A, Steamed at 200° C. (Cofeed H2O) | Example 5 Catalyst A, Steamed at 350° C. (Cofeed H2O) | Example 6 Catalyst A, Steamed at 500° C. (Cofeed H2O) |
|---|---|---|---|
| $X_{Toluene}$ | 13.6 | 12.8 | 9.5 |
| $S_{Mixed-Xylenes}$ | 96.6 | 96.5 | 96.8 |
| $S_{P-Xylene}$ | 89.8 | 89.7 | 88.0 |
| $S_{Methanol}$ | 67.4 | 66.5 | 59.9 |

Examples 7-8

The effect of catalyst steaming was examined on Catalyst B. In all cases, the catalyst was first dried at 200° C. for an hour under hydrogen gas flow. In Example 7, the catalyst was not pre-steamed. In Example 8, after drying the catalyst it was then steamed overnight by flowing hydrogen gas containing from 10-12 mole % H₂O at 200° C. The same reaction conditions as those of Example 4 were used. The results are summarized in Table 3 below.

TABLE 3

| Conversion/Selectivity, mole % | Example 7 Catalyst B, Non-steamed, (Cofeed H2O) | Example 8 Catalyst B, Steamed at 200° C., (Cofeed H2O) |
|---|---|---|
| $X_{Toluene}$ | 12.1 | 15.0 |
| $S_{Mixed-Xylenes}$ | 97.0 | 97.0 |
| $S_{P-Xylene}$ | 91.4 | 90.0 |
| $S_{Methanol}$ | 62.7 | 73.1 |

Examples 9-10

The effect of catalyst steaming was also examined on Catalyst C. In all cases, the catalyst was first dried at 200° C. for an hour under hydrogen gas flow. In Example 9, the catalyst was not pre-steamed, whereas in Example 10, after drying the catalyst it was then steamed overnight by flowing hydrogen gas containing from 10-12 mole % H₂O at 200° C. The same reaction conditions as those of Example 4 using a water cofeed were used. The results are summarized in Table 4 below.

TABLE 4

| Conversion/Selectivity | Example 9 Catalyst C, Non-steamed, (Cofeed H2O) | Example 10 Catalyst C, Steamed at 200° C., (Cofeed H2O) |
|---|---|---|
| $X_{Toluene}$ | 13.4 | 14.2 |
| $S_{Mixed-Xylenes}$ | 98.2 | 98.2 |

TABLE 4-continued

| Conversion/Selectivity | Example 9 Catalyst C, Non-steamed, (Cofeed H2O) | Example 10 Catalyst C, Steamed at 200° C., (Cofeed H2O) |
|---|---|---|
| $S_{P-Xylene}$ | 96.3 | 95.8 |
| $S_{Methanol}$ | 64.8 | 66.0 |

Example 11

The $^{27}$Al MAS NMR spectra were recorded for P-modified ZSM-5 catalyst (e.g., catalyst A). Steaming was carried out by placing about 5.4 ml of sized catalyst (20-40 mesh) in a stainless steel reactor. The catalyst was dried at 200° C. under H₂ or N₂ flow at 50 cc/min for at least one hour. The gas flow was increased to 459 cc/min, and liquid water was introduced at 0.04 ml/min through a vaporizer at 200° C. The reactor temperature was then increased to desired steaming temperature and steaming was continued usually for overnight. Referring to FIG. 1, $^{27}$Al MAS-NMR spectrum of non-steamed catalyst showed a weak peak at 50-55 ppm attributed to the zeolite framework aluminum. A strong peak was observed at around −12 ppm assigned to extra framework aluminum (EFAl). The $^{27}$Al MAS NMR of catalyst A after steaming at 610° C. (for 13 days), showed no or little change in framework Al or EFAl.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of treating a ZSM-5-type zeolite catalyst comprising:
    treating a ZSM-5 zeolite catalyst having a silica/alumina mole ratio of at least about 200 with a phosphorus compound;
    calcining the phosphorus treated ZSM-5 zeolite catalyst; and
    steaming the phosphorus treated ZSM-5 zeolite catalyst with steam at a temperature of less than about 300° C., and wherein the phosphorus treated ZSM-5 zeolite catalyst has less than 0.05% by weight of the catalyst of any other element other than phosphorus provided from any treatment of the ZSM-5 zeolite with a compound containing said other element.

2. The method of claim 1, wherein:
    the phosphorus treated ZSM-5 zeolite catalyst has a phosphorus content of at least about 0.08 g P/g zeolite.

3. The method of claim 1, wherein:
    the phosphorus treated ZSM-5 zeolite catalyst has a phosphorus content of from at least about 0.08 g P/g zeolite to about 0.15 g P/g zeolite.

4. The method of claim 1, wherein:
    the ZSM-5 zeolite catalyst has a silica/alumina mole ratio of at least about 250.

5. The method of claim 1, wherein:
    the phosphorus treated ZSM-5 zeolite catalyst is steamed at a temperature of less than about 250° C.

6. The method of claim 1, wherein:
    the phosphorus treated ZSM-5 zeolite catalyst is steamed at a temperature of from about 150° C. to about 250° C.

7. The method of claim 1, wherein:
    the phosphorus treated ZSM-5 zeolite catalyst is calcined at a temperature of at least about 300° C.

* * * * *